(12) United States Patent
Kellett et al.

(10) Patent No.: US 9,452,422 B2
(45) Date of Patent: Sep. 27, 2016

(54) CATALYSTS AND PROCESSES FOR THE PRODUCTION OF AROMATIC COMPOUNDS FROM LIGNIN

(71) Applicant: The Procter & Gamble Company, Cincinnati, OH (US)

(72) Inventors: Patti Jean Kellett, Cincinnati, OH (US); Dimitris Ioannis Collias, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 56 days.

(21) Appl. No.: 13/796,070

(22) Filed: Mar. 12, 2013

(65) Prior Publication Data

US 2014/0275468 A1    Sep. 18, 2014

(51) Int. Cl.
| | | |
|---|---|---|
| *B01J 29/67* | (2006.01) | |
| *B01J 23/42* | (2006.01) | |
| *B01J 23/44* | (2006.01) | |
| *B01J 23/72* | (2006.01) | |
| *B01J 23/755* | (2006.01) | |
| *B01J 23/835* | (2006.01) | |
| *B01J 29/44* | (2006.01) | |
| *B01J 29/46* | (2006.01) | |
| *C07C 1/22* | (2006.01) | |
| *C07C 37/50* | (2006.01) | |
| *B01J 23/58* | (2006.01) | |
| *B01J 37/18* | (2006.01) | |
| *B01J 23/847* | (2006.01) | |
| *B01J 23/62* | (2006.01) | |
| *B01J 23/648* | (2006.01) | |
| *B01J 23/652* | (2006.01) | |
| *B01J 23/78* | (2006.01) | |
| *B01J 23/86* | (2006.01) | |
| *B01J 29/68* | (2006.01) | |
| *B01J 37/02* | (2006.01) | |

(52) U.S. Cl.
CPC .............. *B01J 29/67* (2013.01); *B01J 23/42* (2013.01); *B01J 23/44* (2013.01); *B01J 23/72* (2013.01); *B01J 23/755* (2013.01); *B01J 23/835* (2013.01); *B01J 29/44* (2013.01); *B01J 29/46* (2013.01); *C07C 1/22* (2013.01); *C07C 37/50* (2013.01); *B01J 23/58* (2013.01); *B01J 23/626* (2013.01); *B01J 23/6482* (2013.01); *B01J 23/6522* (2013.01); *B01J 23/78* (2013.01); *B01J 23/8472* (2013.01); *B01J 23/86* (2013.01); *B01J 29/68* (2013.01); *B01J 37/0201* (2013.01); *B01J 37/18* (2013.01); *C07C 2521/04* (2013.01); *C07C 2529/44* (2013.01); *C07C 2529/46* (2013.01); *Y02P 20/52* (2015.11)

(58) Field of Classification Search
CPC .......... B01J 29/67; B01J 29/46; B01J 29/44; B01J 23/42; B01J 23/44; B01J 23/72; C07C 1/22; C07C 37/50
USPC ......................................................... 585/469
See application file for complete search history.

(56) References Cited

U.S. PATENT DOCUMENTS

| | | |
|---|---|---|
| 3,885,155 A | 5/1975 | Anbar |
| 4,427,884 A | 1/1984 | Anbar et al. |
| 4,605,790 A | 8/1986 | Wojtkowski |
| 4,973,841 A | 11/1990 | Purser |
| 5,438,194 A | 8/1995 | Koudijs et al. |
| 5,661,299 A | 8/1997 | Purser |
| 2009/0227823 A1* | 9/2009 | Huber et al. .................. 585/324 |
| 2012/0101318 A1* | 4/2012 | Ramirez Corredores et al. ............................ 585/240 |
| 2014/0107306 A1* | 4/2014 | Mazanec et al. ............. 526/346 |

FOREIGN PATENT DOCUMENTS

WO    WO 2009/155086 A2    12/2009

OTHER PUBLICATIONS

Chron et al. Recent Advances and New Horizons in Zeolite Science and Technology. Elsevier Science 1996. p. 340.*
Khouw et al. Shape-Selective Catalysis with Zeolites and Molecular Sieves. Chapter 14. American Chemical Society. 1993.*
Tang et al. Shape-Selective and Acid Catalyzed Alkylation of Phenol with Isobutylene Over Zeolite Beta. Studies in Surface Science and Catalysis, vol. 154. 2004.*
Zhu et al., "Bi functional transalkylation and hydrodeoxygenation of anisole over a Pt/HBeta catalyst", Journal of Catalysis 281 (2011) 21-29.
Prasomsri, T.; et al., Catalytic conversion of anisole over HY and HZSM-5 zeolites in the presence of different hydrocarbon mixtures, . Applied Catalysis B: Environmental 2011, 106(1-2), 204-211.
Runnebaum, Ron C., et al., "Catalytic Conversion of Anisole: Evidence of Oxygen Removal in Reactions with Hydrogen", Catal Lett (2011) 141:817-820.
Nimmanwudipong, Tarit et al., "Catalytic Conversion of Guaiacol Catalyzed by Platinum Supported on Alumina: Reaction Network Including Hydrodeoxygenation Reactions", Energy & Fuels 2011, 25, 3417-3427.

(Continued)

*Primary Examiner* — John Uselding
(74) *Attorney, Agent, or Firm* — Brent M. Peebles

(57) ABSTRACT

Hydrotreating catalysts and processes useful for the conversion of methoxylated aromatic compounds to simple aromatic compounds are provided. The catalysts comprise transition metal selected from the group consisting of Group 8 metals, Group 9 metals, Group 10 metals, Group 11 metals, and mixtures thereof, and catalyst support selected from the group consisting of shape-selective zeolite, silica, titania, zirconia, and mixtures thereof.

7 Claims, No Drawings

(56) References Cited

OTHER PUBLICATIONS

Designation D6556-10—Standard Test Method for Carbon Black—Total and External Surface Area by Adsorption, ASTM International, pp. 1-5.

Designation D6866-10—Standard Test Methods for Determining the Biobased Content of Solid, Liquid, and Gaseous Samples Using Radiocarbon Analysis ASTM International, pp. 1-15.

Bozell, JJ et al., "Top Value-Added Chemical from Biomass—vol. II—Results of Screening for Potential Candidates from Biorefinery Lignin"—Pacific Northwest National Lab., Oct. 2007, pp. 1-87.

Deutsch, K., et al,. "Hydrodeoxygenation of lignin model compounds over a copper chromite catalyst", Applied Catalysis A: General 447-448 (2012) 144-150.

Pandey, M. et al., "Lignin Depolymerization and Conversion: A Review of Thermochemical Methods", Chem. Eng. Technol. 2011, 34, No. 1, 29-41.

Kirk-Othmer Encyclopedia of Chemical Technolgy, vol. 15, pp. 1-32, 2001.

International Search Report and Written Opinion dated May 28, 2014.

\* cited by examiner

CATALYSTS AND PROCESSES FOR THE PRODUCTION OF AROMATIC COMPOUNDS FROM LIGNIN

FIELD OF THE INVENTION

The present invention generally relates to catalysts and processes useful for the conversion of methoxylated aromatic compounds to simple aromatic compounds. More specifically, the invention relates to catalysts and processes useful for the hydrotreating of depolymerized lignin compositions to simple aromatic compounds, such as, benzene, toluene, and xylenes with high yield, selectivity, and conversion.

BACKGROUND OF THE INVENTION

Lignin is one of the three basic components of lignocellulosic biomass, the other two being cellulose and hemicellulose. On a dry basis, lignin is about 17 wt %-33 wt % of the biomass and about 40% of its energy (27 wt % to 33 wt % in softwoods, 18 wt % to 25 wt % in hardwoods, and 17 wt % to 24 wt % in grasses; Bozell, et al., Top Value Added Chemicals from Biomass—Volume II, PNNL—16983, 2007), whereas cellulose and hemicellulose together are about 60 wt %-85 wt % of the biomass. Lignin is a natural, amorphous, cross-linked three-dimensional polyphenolic compound. Although the exact structure of lignin is complex and changes depending on which biomass it is part of, in general terms, lignin contains phenylpropenyl (C9) branched units connected to each other with either carbon-carbon or carbon-oxygen (ether) bonds of the type β-O-4, 5-5, β-5, β-1, α-O-4,4-O-5, β-β, etc. Lignin is the only biomass polymer that contains aromatic units, and it is estimated that about 40 wt % of lignin is aromatic. Lignin is made naturally by enzymatic polymerization of coniferyl alcohol, sinapyl alcohol, and para-coumaryl alcohol. These alcohols are essentially the monomeric units in lignin. Coniferyl alcohol (4-(3-hydroxy-1-propenyl)-2-methoxyphenol) has one —OH (hydroxy) group, one —$OCH_3$ (methoxy) group, and one —CH=$CHCH_2OH$ (hydroxypropenyl) group; sinapyl alcohol (4-(3-hydroxyprop-1-enyl)-2,6-dimethoxyphenol) has one —OH group, two —$OCH_3$ groups, and one —CH=$CHCH_2OH$ group; and para-coumaryl alcohol (4-(3-hydroxy-1-propenyl)phenol)) has one —OH group and one —CH=$CHCH_2OH$ group. Thus, the monomeric units in lignin have phenolic hydroxy, hydroxypropenyl, and methoxy pendant groups from an aromatic ring, with the methoxy groups being the most abundant per 100 C9 units (e.g. about 95 methoxy pendant groups per 100 C9 units in softwood lignin).

The global production of lignin today is about 1 million tons, and it comes in various forms as a by-product of pulp and paper operations. One form of lignin is kraft lignin, which is produced from the sulfate pulping process, has a molecular weight of 2,000 to 3,000 g/mol, and has an average molecular weight of the monomeric unit of 180 g/mol. Another form of lignin is lignosulfonate, which is produced from the sulfite pulping process, has a molecular weight of 20,000 to 50,000 g/mol, and has an average molecular weight of the monomeric unit of 215 to 254 g/mol. A third form of lignin is organosolv lignin, which is produced from the alcohol pulping process, has a molecular weight of less than 1,000 g/mol, and an average molecular weight of the monomeric unit of 188 g/mol (Lebo et al., Kirk-Othmer Encyclopedia of Chemical Technology, Online Edition, J. Wiley & Sons, 2001). Main uses of lignin today are for power generation, detergents, dispersants, additives, raw materials for vanillin, humic acid, etc., dust suppression agents, etc.

Lignin is expected to be produced in much larger quantities in the future as many companies are commercializing cellulosic sugars and ethanol, and lignin becomes a by-product of these operations. For example, in a recent study, the US DoE suggested that 1.3 billion tons of biomass is available annually in the US for biofuels and biomaterials. This amount of biomass could yield about 400 million tons of lignin annually. Converting this large amount of lignin to high-value and/or high-volume chemicals and fuels (e.g. phenol, benzene, toluene, xylenes, etc.), which today are made from petroleum or natural gas sources, could help the environmental profile of these chemicals, as well as could lower their production cost. Additionally, this use of lignin could help lower the final price of cellulosic sugars and ethanol, which will be co-produced in a bio-refinery type of operation.

To convert lignin or bio-oils from a fast pyrolysis process, to chemicals such as, benzene, toluene, and xylenes, one has to remove oxygen and add hydrogen, i.e., to perform a hydrotreating reaction. In the petroleum industry, catalysts have been used for a similar hydrotreating operation, called hydrotreating, where sulfur or nitrogen are removed via hydrodesulfurization (HDS) and hydrodenitrogenation (HDN), respectively. Similar catalysts have been proposed for hydrotreating of lignin compounds or model monomers. However, these HDS catalysts are not stable in water or alcohol solvents, showed poor conversion in hydrotreating environments, required co-feeding of $H_2S$ to maintain their activity, and exhibited high costs (Deutsch, K. L., and B. H. Shanks, Applied Catalysis A: General, 447-448, 144-150 (2012)).

Accordingly, there is a need for processes and catalysts for the conversion of methoxylated aromatic compounds, including depolymerized lignin compounds, to simple aromatic compounds with high yield, selectivity, and efficiency (i.e., short residence time), and high longevity catalysts.

SUMMARY OF THE INVENTION

In one embodiment, a process for the conversion of methoxylated aromatic compounds and compositions comprising methoxylated aromatic compounds to simple aromatic compounds is provided. The process comprises the step of bringing the methoxylated aromatic compounds and compositions comprising methoxylated aromatic compounds in contact with a catalyst and hydrogen in a reactor, wherein the catalyst comprises: a) a transition metal selected from the group consisting of Group 8 metals, Group 9 metals, Group 10 metals, Group 11 metals, and mixtures thereof; and b) a catalyst support selected from the group consisting of shape-selective zeolite, silica, titania, zirconia, and mixtures thereof.

In another embodiment, a process for the conversion of methoxylated aromatic compounds and compositions comprising methoxylated aromatic compounds to simple aromatic compounds is provided. The process comprises the step of bringing the methoxylated aromatic compounds and compositions comprising methoxylated aromatic compounds in contact with a catalyst and hydrogen in a reactor, wherein the catalyst comprises: a) a transition metal selected from the group consisting of Group 8 metals, Group 9 metals, Group 10 metals, Group 11 metals, and mixtures thereof; b) a promoter metal; and c) an alumina catalyst support.

In another embodiment of the present invention, a process for the conversion of a composition of depolymerized lignin to simple aromatic compounds is provided. The process comprises the step of bringing the composition of depolymerized lignin in contact with a catalyst and about 32 molar equivalents of hydrogen in a flow reactor, wherein the catalyst comprises Ni deposited onto ferrierite zeolite; and wherein the flow reactor has a temperature of about 350° C., a pressure of about 370 psig, and an LHSV of about 3 h$^{-1}$.

In yet another embodiment of the present invention, a process for the conversion of a composition of depolymerized lignin to simple aromatic compounds is provided. The process comprises the step of bringing the composition of depolymerized lignin in contact with a catalyst and about 32 molar equivalents of hydrogen in a flow reactor, wherein the catalyst comprises Pt deposited onto H-ZSM-5 zeolite; and wherein the flow reactor has a temperature of about 350° C., a pressure of about 370 psig, and an LHSV of about 3 h$^{-1}$.

In even yet another embodiment of the present invention, a process for the conversion of a composition of depolymerized lignin to simple aromatic compounds is provided. The process comprises the step of bringing the composition of depolymerized lignin in contact with a catalyst and about 32 molar equivalents of hydrogen in a flow reactor, wherein the catalyst comprises Pd and Cr deposited onto silica; and wherein the flow reactor has a temperature of about 350° C., a pressure of about 370 psig, and an LHSV of about 3 h$^{-1}$.

In another embodiment of the present invention, a poly (ethylene terephthalate) resin is produced from monoethylene glycol and terephthalic acid, wherein the terephthalic acid is produced from para-xylene; wherein the para-xylene is produced from lignin; and wherein the poly(ethylene terephthalate) resin has a bio-based content greater than about 30%.

In yet another embodiment of the present invention, a process for the conversion of lignin to BTX is provided. The process comprises the steps of: a) depolymerization of the lignin to produce a depolymerized lignin composition; b) hydrotreating the depolymerized lignin composition to produce simple aromatic compounds; and c) aromatic dealkylation of the simple aromatic compounds to produce said BTX.

DETAILED DESCRIPTION OF THE INVENTION

I Definitions

As used herein, the term "lignocellulosic material" refers to a material comprising lignin, cellulose, and hemicellulose.

As used herein, the term "methoxylated aromatic compounds" refers to aromatic compounds that have a methoxy group pendant from the aromatic ring, and optionally at least one other pendant group from the aromatic ring. Non-limiting examples of the other pendant group from the aromatic ring are hydroxyl, methoxy, methyl, ethyl, propyl, and allyl (2-propenyl). Non-limiting examples of methoxylated aromatic compounds are methoxybenzene (anisole), 2,6-dimethoxyphenol (syringol), 4-allyl-2-methoxyphenol (eugenol), 2-methoxyphenol (guaiacol), coniferyl alcohol, and sinapyl alcohol.

As used herein, the term "simple aromatic compounds" refers to phenol, benzene, toluene (methyl benzene), ethyl benzene, propyl benzene, xylenes (ortho-, meta-, and para-dimethyl benzene compounds), and various dialkyl substituted benzene compounds, such as the isomeric methylethyl benzene.

As used herein, the term "BTX" refers collectively to benzene, toluene, and xylenes (i.e., ortho-xylene, meta-xylene, and para-xylene).

As used herein, the term "shape-selective zeolite" refers to a zeolite which exhibits differences in selectivity for the specific catalytic processes (such as diffusion, adsorption, and desorption) of this invention because of differences in the size and shape of the molecules. For the purpose of this invention, the shape-selective zeolite has 10-rings and pore sizes up to 0.60 nm. Non-limiting examples of such shape-selective zeolite is H-ZSM-S and ferrierite.

As used herein, the term "lignin monomers" refers to compounds selected from the group consisting of para-coumaryl alcohol, sinapyl alcohol, coniferyl alcohol, their derivatives, and mixtures thereof.

As used herein, the term "lignin oligomers" refers to lignin compounds that contain a few (i.e., from 2 to about 10) lignin monomers.

As used herein, the term "lignin fragments" refers to segments of lignin produced during the lignin depolymerization process using any method known to those skilled in the art.

As used herein, the term "depolymerized lignin composition" refers to a composition comprising lignin oligomers, lignin monomers, and lignin fragments, which are produced by breaking down lignin using any method known to those skilled in the art.

As used herein, the term "hydrogen molar equivalents" refers to the molar ratio of molecular hydrogen ($H_2$, molecular weight is 2 g/mol) and syringol (molecular weight is 154 g/mol) present in the composition as a single chemical compound. If syringol is not the only methoxylated aromatic compound present or not present at all in the composition, then the equivalent amount of moles of syringol is calculated and used. The equivalent amount of moles of syringol is calculated by dividing the total weight of the methoxylated aromatic compounds in the composition with the molecular weight of syringol.

As used herein, the term "bio-based material" refers to a renewable material.

As used herein, the term "renewable material" refers to a material that is produced from a renewable resource.

As used herein, the term "renewable resource" refers to a resource that is produced via a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulose, hemicellulose, cellulosic waste), animals, fish, bacteria, fungi, and forestry products. These resources can be naturally occurring, hybrids, or genetically engineered organisms. Natural resources, such as crude oil, coal, natural gas, and peat, which take longer than 100 years to form, are not considered renewable resources. Because at least part of the material of the invention is derived from a renewable resource, which can sequester carbon dioxide, use of the material can reduce global warming potential and fossil fuel consumption.

As used herein, the term "bio-based content" refers to the amount of carbon from a renewable resource in a material as a percent of the weight (mass) of the total organic carbon in the material, as determined by ASTM D6866-10 Method B.

As used herein, the term "petroleum-based" material refers to a material that is produced from fossil material, such as petroleum, natural gas, coal, etc.

As used herein, the term "particle span" refers to a statistical representation of a given particle sample and is equal to $(D_{v,0.90}-D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.90}$, is the particle size that separates the particle sample at the 90% by volume fraction.

As used herein, the term "conversion" in % is defined as [lignin compounds flow rate in (mol/min)−lignin compounds flow rate out (mol/min)]/[lignin compounds flow rate in (mol/min)]*100. For the purposes of this invention, the term "conversion" means molar conversion, unless otherwise noted.

As used herein, the term "yield" in % is defined as [product flow rate out (mol/min)/lignin compounds flow rate in (mol/min)]*100. For the purposes of this invention, the term "yield" means molar yield, unless otherwise noted.

As used herein, the term "selectivity" in % is defined as [Yield/Conversion]*100. For the purposes of this invention, the term "selectivity" means molar selectivity, unless otherwise noted.

As used herein, the term "Liquid Hourly Space Velocity" or "LHSV" in $h^{-1}$ is defined as 60×[Total liquid flow rate (mL/min)/catalyst bed volume (mL)].

As used herein, the term "NmL/min" refers to volumetric flow rate in mL/min calculated under Standard Pressure and Temperature conditions (STP; 0° C. and 1 atm).

As used herein, the term "total pore volume" refers to the volume of all the intra-particle pores, i.e., micropores, mesopores, and macropores. The total pore volume is calculated as the volume of nitrogen adsorbed at a relative pressure of 0.9814 using the BET process (ASTM D 4820-99 standard), which is well known in the art.

II Catalysts and Processes

Unexpectedly it was found that catalysts with a transition metal selected from the group consisting of Group 8 metals, Group 9 metals, Group 10 metals, Group 11 metals, or mixtures thereof, and shape-selective zeolite or silica as support allow the use of water or alcohol and water mixed solvents in the conversion of methoxylated aromatic compounds or lignin to simple aromatic compounds with high yield, selectivity, and conversion; and without the loss of activity. Unlike traditional hydrodesulfurization catalysts or hydrotreating catalysts, these catalysts did not require the use of $H_2S$ or an organic solvent, thus improving the safety profile of the conversion.

In one embodiment of the present invention, a process for the conversion of a composition comprising methoxylated aromatic compounds to simple aromatic compounds comprises the step of bringing the composition comprising methoxylated aromatic compounds in contact with a catalyst and hydrogen in a reactor, wherein the catalyst comprises: a) a transition metal selected from the group consisting of Group 8 metals, Group 9 metals, Group 10 metals, Group 11 metals, and mixtures thereof; and b) a catalyst support selected from the group consisting of shape-selective zeolite, silica, titania, zirconia, and mixtures thereof.

In another embodiment, a process for the conversion of methoxylated aromatic compounds and compositions comprising methoxylated aromatic compounds to simple aromatic compounds is provided. The process comprises the step of bringing the composition comprising methoxylated aromatic compounds and compositions comprising methoxylated aromatic compounds in contact with a catalyst and hydrogen in a reactor, wherein the catalyst comprises: a) a transition metal selected from the group consisting of Group 8 metals, Group 9 metals, Group 10 metals, Group 11 metals, and mixtures thereof; b) a promoter metal; and c) an alumina catalyst support.

In another embodiment, the methoxylated aromatic compounds comprise a depolymerized lignin composition, which comprises lignin monomers, lignin oligomers, and lignin fragments, which are produced by breaking down lignin using any method known to those skilled in the art. Non-limiting examples of processes that produce lignin are kraft, sulfite, organosolv, pyrolysis, steam explosion, dilute acid, alkaline oxidation, hot water, alkaline, and ammonia fiber explosion (AFEX). These processes have been applied to hardwoods, softwoods, and agricultural residues, with varying degrees of success. Furthermore, depolymerized lignin compositions can be achieved using a variety of methods, such as, by way of example and not limitation, lignin pyrolysis, gasification, hydrogenolysis, oxidation, and hydrolysis under supercritical conditions (see Pandey et al., Chem. Eng. Technol., 34, 29 (2011)).

In another embodiment, the depolymerized lignin composition comprises lignin oligomers. The lignin oligomers can contain 2 to about 10 lignin monomers connected together. In yet another embodiment, the depolymerized lignin composition comprises lignin monomers, such as, para-coumaryl alcohol, coniferyl alcohol, and sinapyl alcohol; or their derivatives. Non-limiting examples of lignin monomer derivatives are compounds in which the hydroxyl groups of para-coumaryl, coniferyl, and sinapyl alcohols are esterified with simple carboxylic acids, such as acetic and propanoic acid, or in which the unsaturated hydroxypropenyl side chains of para-coumaryl, coniferyl, and sinapyl alcohols are reduced to give propyl side chains.

The simple aromatic compounds, which are produced from the composition of methoxylated aromatic compounds, include phenol, benzene, toluene (methyl benzene), ethyl benzene, propyl benzene, xylenes, and various dialkyl substituted benzene compounds, such as the isomeric methyl-ethyl benzene. These simple aromatic compounds include compounds that have very important commercial value such as, for example, phenol and BTX, and other compounds that can be dealkylated to benzene, among other compounds. A potential use of bio-based benzene is in the same areas as petroleum-based benzene is used today, such as, production of styrene, phenol, nylon, and linear alkyl benzene sulfonate (LAS) surfactants. Bio-based para-xylene can be used to produce bio-based terephthalic acid (using the same process currently used to convert petroleum-based para-xylene to terephthalic acid). The bio-based terephthalic acid can then be used to make poly(ethylene terephthalate) when combined with either petroleum-based monoethylene glycol or bio-based monoethylene glycol.

The methoxylated aromatic compounds are converted to simple aromatic compounds by bringing them in contact with a catalyst and hydrogen in a reactor. The catalyst comprises a transition metal selected from the group consisting of Group 8 metals, Group 9 metals, Group 10 metals, Group 11 metals, and mixtures thereof. In one embodiment, the transition metal is selected from the group consisting of Fe, Ru, Co, Rh, Ni, Pd, Pt, Cu, and mixtures thereof. In another embodiment, the transition metal is selected from the group consisting of Ni, Pd, Pt, Cu, and mixtures thereof.

In one embodiment, the transition metal is less than about 20 wt % of the total catalyst weight. In another embodiment, the transition metal is less than about 5 wt % of the total catalyst weight.

The catalyst also comprises a catalyst support. In one embodiment, the catalyst support is selected from the group consisting of shape-selective zeolite, silica, titania, zirconia, and mixtures thereof. In another embodiment, the shape-selective zeolite comprises ferrierite zeolite or H-ZSM-5 zeolite. Typically, ferrierite zeolite has a chemical formula $(Na,K)_2Mg(Si,Al)_{18}O_{36}(OH).9H_2O$, and H-ZSM-5 zeolite has a chemical formula $Na_nAl_nSi_{96-n}O_{192}.16H_2O$ ($0<n<27$).

In one embodiment, the BET surface area of the catalyst support is between about 60 m²/g and about 750 m²/g. In another embodiment, the BET surface area of the catalyst support is about 250 m²/g. In one embodiment, the total pore volume of the catalyst support is between about 0.4 mL/g and about 3.2 mL/g. In another embodiment, the total pore volume of the catalyst support is about 0.9 m²/g.

The catalyst support can also comprise a promoter metal, which typically increases the activity of the catalyst although it is not a catalyst by itself. In one embodiment, the promoter metal is selected from the group consisting of Mg, V, Cr, Sn, and mixtures thereof. In another embodiment, the promoter metal is Mg. In one embodiment, the promoter metal is less than about 10 wt % of the total catalyst weight. In another embodiment, the promoter metal is less than about 5 wt % of the total catalyst weight. In yet another embodiment, the promoter metal is about 2 wt % of the total catalyst weight.

The hydrogen gas is used in an amount calculated as molar equivalents with respect to the number of moles of a specific methoxylated aromatic compound which is converted to simple aromatic compounds in the process. As stated in Section I, the specific methoxylated aromatic compound is syringol with molecular weight to 154 g/mol, if syringol is the only methoxylated aromatic compound present in the composition. If syringol is not the only methoxylated aromatic compound present or not present at all in the composition, then the equivalent amount of moles of syringol is calculated and used. The equivalent amount of moles of syringol is calculated by dividing the total weight of the methoxylated aromatic compounds in the composition with the molecular weight of syringol. In one embodiment, about 2 to about 128 molar equivalents of hydrogen are used. In another embodiment, about 4 to about 96 molar equivalents of hydrogen are used. In yet another embodiment, about 8 to about 64 molar equivalents of hydrogen are used. In even yet another embodiment, about 32 molar equivalents of hydrogen are used.

In one embodiment, the hydrogen gas comprises an inert gas (i.e., a gas otherwise inert to the reaction mixture under the conditions of the method). Non-limiting examples of the inert gas are nitrogen, air, helium, argon, carbon dioxide, carbon monoxide, steam, and mixtures thereof. In another embodiment, the inert gas is nitrogen.

The conversion of the composition of methoxylated aromatic compounds to simple aromatic compounds can be performed in a reactor, which can be operated in batch form or continuous form. In one embodiment, the conversion is performed in a flow reactor. The conversion can be performed in the reactor with the composition flowing down, or flowing up, or flowing horizontally. In one embodiment, the conversion is performed in a reactor with the composition flowing down.

In one embodiment, the temperature in the reactor is between about 200° C. and about 500° C. In another embodiment, the temperature in the reactor is between about 250° C. and about 400° C. In yet another embodiment, the temperature in the reactor is between about 300° C. and about 375° C. In one embodiment, the pressure in the reactor is between about 15 psig and about 3,700 psig. In another embodiment, the pressure in the reactor is between about 150 psig and about 500 psig. In yet another embodiment, the pressure in the reactor is about 370 psig.

The LHSV of the composition of methoxylated aromatic compounds in the flow reactor is less than about 3,600 $h^{-1}$. In one embodiment, the LHSV of the composition of methoxylated aromatic compounds in the flow reactor is less than about 1,800 $h^{-1}$. In another embodiment, the LHSV of the composition of methoxylated aromatic compounds in the flow reactor is less than about 360 $h^{-1}$. In yet another embodiment, the LHSV of the composition of methoxylated aromatic compounds in the flow reactor is less than about 10 $h^{-1}$. In one embodiment, the LHSV of the composition of methoxylated aromatic compounds in the flow reactor is about 3 $h^{-1}$. In another embodiment, the LHSV of the composition of methoxylated aromatic compounds in the flow reactor is about 1.5 $h^{-1}$.

In one embodiment, the bio-based content of the simple aromatic compounds is greater than about 3%. In another embodiment, the bio-based content of the simple aromatic compounds is greater than about 30%. In yet another embodiment, the bio-based content of the simple aromatic compounds is greater than about 90%.

In one embodiment of the present invention, a process for the conversion of a composition of depolymerized lignin to simple aromatic compounds is provided. The process comprises the step of bringing the composition of depolymerized lignin in contact with a catalyst and about 32 molar equivalents of hydrogen in a flow reactor, wherein the catalyst comprises Ni deposited onto ferrierite zeolite; and wherein the flow reactor has a temperature of about 350° C., a pressure of about 370 psig, and an LHSV of about 3 $h^{-1}$.

In another embodiment of the present invention, a process for the conversion of a composition of depolymerized lignin to simple aromatic compounds is provided. The process comprises the step of bringing the composition of depolymerized lignin in contact with a catalyst and about 32 molar equivalents of hydrogen in a flow reactor, wherein the catalyst comprises Pt deposited onto H-ZSM-5 zeolite; and wherein the flow reactor has a temperature of about 350° C., a pressure of about 370 psig, and an LHSV of about 3 $h^{-1}$.

In yet another embodiment of the present invention, a process for the conversion of a composition of depolymerized lignin to simple aromatic compounds is provided. The process comprises the step of bringing the composition of depolymerized lignin in contact with a catalyst and about 32 molar equivalents of hydrogen in a flow reactor, wherein the catalyst comprises Pd and Cr deposited onto silica; and wherein the flow reactor has a temperature of about 350° C., a pressure of about 370 psig, and an LHSV of about 3 $h^{-1}$.

In one embodiment of the present invention, a poly(ethylene terephthalate) resin is produced from monoethylene glycol and terephthalic acid, wherein the terephthalic acid is produced from para-xylene; wherein the para-xylene is produced from lignin; and wherein the poly(ethylene terephthalate) resin has a bio-based content greater than about 30%. In another embodiment, a poly(ethylene terephthalate) resin is produced from monoethylene glycol and terephthalic acid, wherein the terephthalic acid is produced from para-xylene; wherein the para-xylene is produced from lignin; and wherein the poly(ethylene terephthalate) resin has a bio-based content greater than about 90%.

In one embodiment of the present invention, a process for the conversion of lignin to BTX is provided. The process comprises the steps of: a) depolymerization of the lignin to produce a depolymerized lignin composition; b) hydrotreating the depolymerized lignin composition to produce simple aromatic compounds; and c) aromatic dealkylation of the simple aromatic compounds to produce said BTX. In another embodiment of the present invention, the hydrotreating step comprises bringing the depolymerized lignin composition in contact with a catalyst and hydrogen in a reactor, wherein the catalyst comprises a transition metal selected from the group consisting of Group 8 metals, Group 9 metals, Group 10 metals, Group 11 metals, and mixtures thereof; and a catalyst support selected from the group consisting of shape-selective zeolite, silica, titania, zirconia, and mixtures thereof.

Aromatic dealkylation is a well known process to those skilled in the art, and a very important process in the petrochemical industry. It involves a catalytic process that uses steam or hydrogen, removes alkyl pendant groups from the aromatic ring, and produces dealkylated aromatic compounds, such as benzene. U.S. Pat. No. 3,649,706 (issued in 1972), U.S. Pat. No. 4,199,436 (issued in 1980), and U.S. Pat. No. 4,268,703 (issued in 1981) are examples of dealkylation processes. Production of benzene from toluene or xylenes, and naphthalene from alkylnaphthalenes are two examples of aromatic dealkylation that is practiced today in the petrochemical industry. Typical process conditions include temperature from about 300° C. to about 700° C., pressure from about 1 barg to about 100 barg, and LHSV less than about 10 $h^{-1}$. More specifically, the dealkylation of toluene to benzene is performed over a chromium, molybdenum, or platinum oxide catalyst at about 500° C. to about 600° C. and pressure from about 40 barg to about 60 barg.

Benzene produced from lignin with the present invention (i.e., bio-based benzene) may be used in typical petroleum-based benzene applications, such as, by way of example and not limitation, production of ethylbenzene, cumene, and cyclohexane. These three chemicals may then be used to produce styrene for plastics, styrene-butadiene rubber (SBR), and styrene copolymers; phenol for resins and adhesives, polycarbonate, Nylon, and epoxy resins; and Nylon, respectively. In one embodiment of the present invention, a linear alkyl benzene sulfonate surfactant (LAS) is produced from benzene, wherein the benzene is produced from lignin. In another embodiment of the present invention, a polystyrene resin is produced from ethylbenzene, wherein the ethylbenzene is produced from benzene, and wherein the benzene is produced from lignin. In yet another embodiment of the present invention, a phenolic resin is produced from cumene, wherein the cumene is produced from benzene, and wherein the benzene is produced from lignin.

In one embodiment of the present invention, the para-xylene from the simple aromatic compounds is converted to terephthalic acid, and wherein the terephthalic acid is further reacted with ethylene glycol to produce poly(ethylene terephthalate) resin. In another embodiment, the para-xylene from the BTX is converted to terephthalic acid, and wherein the terephthalic acid is further reacted with ethylene glycol to produce poly(ethylene terephthalate) resin.

In one embodiment of the present invention, the benzene from the simple aromatic compounds is combined with linear alkenes to produce linear alkylbenzene (LAB) compounds, and wherein the LAB compounds are further sulfonated to produce linear alkylbenzene sulfonate (LAS) surfactants. In another embodiment, the benzene from BTX is combined with linear alkenes to produce linear alkylbenzene (LAB) compounds, and wherein the LAB compounds are further sulfonated to produce linear alkylbenzene sulfonate (LAS) surfactants.

III Examples

The procedures applied as well as the yield of aromatic products under various reaction conditions are provided in the following non-limiting examples, which illustrate the hydrotreating of lignin and depolymerized lignin compounds.

Example 1 (Comparative Catalyst)

A 10 wt % Mo (as $MoS_2$) on alumina catalyst was prepared as follows. 11.46 g of ammonium tetrathiomolybdate (Sigma-Aldrich Co. LLC, St. Louis, Mo.; 99.97% purity, Catalog #332446) were dissolved in 20 mL of ethylene diamine (Alfa Aesar GmbH & Co KG, Karlsruhe, Germany; 99% purity, Catalog #A12132) in a reaction vessel which was placed in an ice bath and the solid was added slowly to avoid a violent reaction upon first addition. The solution was heated for about 30 minutes at about 60° C. and then cooled to room temperature. The solution of the molybdenum precursor was mixed in water, and alumina (dried at about 105° C. for about 18 hours) was impregnated with the solution at about 60° C. The isolated solid was heated under vacuum in a rotary evaporator overnight and then calcined under nitrogen for about 3 hours at about 450° C.

Promoter metals were added to the 10 wt % Mo on alumina catalyst by impregnating them with an appropriate amount of $Ni(NO_3)_2.6H_2O$ (Alfa Aesar GmbH & Co KG, Karlsruhe, Germany; Catalog #12222) or $Co(NO_3)_2.6H_2O$ (Alfa Aesar GmbH & Co KG, Karlsruhe, Germany; Catalog #36418) or $(NH_4)_6H_2W_{12}O_{40}$ (Alfa Aesar GmbH & Co KG, Karlsruhe, Germany; Catalog #44792) as follows. Stock solutions were prepared of the promoter metals in water. The appropriate mixture of stock solutions were added to an impregnation bottle and made up to 5 mL with water; 1.5 g of the calcined 10 wt % Mo on alumina catalyst was added to the impregnation bottle; and the sample was impregnated for about 18 hours while it was mixed. The resulting solid was dried at about 105° C. for about 2 hours and calcined under nitrogen at about 450° C. for about 6 hours. Single promoter, binary, and ternary mixtures were all made that way.

Example 2

A 10 wt % Pt (or Pd or Ni or Cu) on silica catalyst was prepared using wet co-impregnation. Platinum nitrate salt $Pt(NO_3)_2$ (Chempur GmbH, Karlsruhe, Germany; Catalog #6438), or palladium nitrate hydrate salt $Pd(NO_3)_2.xH_2O$ (Alfa Aesar GmbH & Co KG, Karlsruhe, Germany; Catalog #11035), or nickel nitrate hydrate salt $Ni(NO_3)_2.6H_2O$ (Alfa Aesar GmbH & Co KG, Karlsruhe, Germany; Catalog #12222), or copper nitrate hydrate salt $Cu(NO_3)_2.3H_2O$ (Alfa Aesar GmbH & Co KG, Karlsruhe, Germany; Catalog #12523) was added to 2 g of dry silica (Saint-Gobain N or Pro GmbH, Steinefrenz, Germany; Catalog #SS 61138) in 10 mL of water. The slurry was allowed to impregnate overnight while stirring at ambient temperature. After impregnation, the liquid was decanted and the catalyst was dried at about 105° C. for about 4 hours followed by calcination in air at about 320° C. for about 4 hours. The catalyst was reduced in the reactor prior to the test by flowing 5 vol. % $H_2$ in $N_2$ over the catalysts at a temperature of about 320° C. for about 2 hours.

Example 3

A 10 wt % Pt and 2 wt % Mg (as a promoter) on silica catalyst was prepared using wet co-impregnation. Platinum nitrate salt $Pt(NO_3)_2$ (Chempur GmbH, Karlsruhe, Germany; Catalog #6438) and magnesium nitrate hydrate salt $Mg(NO_3)_2 \cdot 6H_2O$ (Alfa Aesar GmbH & Co KG, Karlsruhe, Germany; Catalog #11564) salt were added to 2 g of dry silica support (Saint-Gobain N or Pro GmbH, Steinefrenz, Germany; Catalog #SS 61138) in 10 mL of water. The slurry was impregnated overnight while stirring at ambient temperature. After impregnation, the liquid was decanted and the catalyst was dried at about 105° C. for about 4 hours followed by calcination in air at about 320° C. for about 4 hours. The catalyst was reduced in the reactor prior to the test by flowing 5 vol. % $H_2$ in $N_2$ over the catalyst at a temperature of about 320° C. for about 2 hours.

Example 4

A 10 wt % Pt on ferrierite catalyst was prepared using wet co-impregnation. Platinum nitrate salt $Pt(NO_3)_2$ (Chempur GmbH, Karlsruhe, Germany; Catalog #6438) was added to 2 g of dry ferrierite support (Zeolyst International, Valley Forge, Pa.; Catalog #CP 914C CY(1.6)) in 10 mL of water. The slurry was impregnated overnight while stirring at ambient temperature. After impregnation, the liquid was decanted and the catalyst was dried at about 105° C. for about 4 hours followed by calcination in air at about 320° C. for about 4 hours. The catalyst was reduced in the reactor prior to the test by flowing 5 vol. % $H_2$ in $N_2$ over the catalyst at a temperature of about 320° C. for about 2 hours.

Example 5

A 10 wt % Pt on H-ZSM-S catalyst was prepared using wet co-impregnation. Platinum nitrate salt $Pt(NO_3)_2$ (Chempur GmbH, Karlsruhe, Germany; Catalog #6438) was added to 2 g of dry H-ZSM-5 support (Zeolyst International, Valley Forge, Pa.; Catalog #CBV 3014 CY(1.6)) in 10 mL of water. The slurry was impregnated overnight while stirring at ambient temperature. After impregnation, the liquid was decanted and the catalyst was dried at about 105° C. for about 4 hours followed by calcination in air at about 320° C. for about 4 hours. The catalyst was reduced in the reactor prior to the test by flowing 5 vol. % $H_2$ in $N_2$ over the catalyst at a temperature of about 320° C. for about 2 hours.

Similarly, a 10 wt % Ni on H-ZSM-S catalyst was prepared using nickel nitrate hydrate salt $Ni(NO_3)_2 \cdot 6H_2O$ (Alfa Aesar GmbH & Co KG, Karlsruhe, Germany; Catalog #12222), and a 10 wt % Cu on H-ZSM-S catalyst was prepared using copper nitrate hydrate salt $Cu(NO_3)_2 \cdot 3H_2O$ (Alfa Aesar GmbH & Co KG, Karlsruhe, Germany; Catalog #12523).

Example 6

A 10 wt % Ni and 2 wt % Sn (as a promoter) on alumina catalyst was prepared using wet co-impregnation. Nickel nitrate hydrate salt $Ni(NO_3)_2 \cdot 6H_2O$ (Alfa Aesar GmbH & Co KG, Karlsruhe, Germany; Catalog #12222) and tin acetate $Sn(OAc)_2$ (Alfa Aesar GmbH & Co KG, Karlsruhe, Germany; Catalog #22361) salt were added to 2 g of dry alumina support (Saint-Gobain N or Pro GmbH, Steinefrenz, Germany; Catalog #SA 6173) in 10 mL of water. The slurry was impregnated overnight while stirring at ambient temperature. After impregnation, the liquid was decanted and the catalyst was dried at about 105° C. for about 4 hours followed by calcination in air at about 320° C. for about 4 hours. The catalyst was reduced in the reactor prior to the test by flowing 5 vol. % $H_2$ in $N_2$ over the catalyst at a temperature of about 320° C. for about 2 hours.

Example 7 (Comparative)

A 5 wt % solution of anisole (Sigma-Aldrich Co. LLC, St. Louis, Mo.; 99.7% purity; Catalog #296295) in ethanol was fed into the reactor (see reactor details in Section IV) with a 100 □L bed of the 10 wt % Mo and 1 wt % W promoter on alumina catalyst, prepared as in Example 1, at an LHSV of about 3 $h^{-1}$. The feed was stabilized for about 1 hour at about 22° C. before the temperature was raised to about 250° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent was sent to waste. The effluent was subsequently collected for a period of about 16 hours and analyzed by GC to give an average product distribution over the run time. The product contained about 25 vol. % phenol and about 55 vol. % anisole.

Example 8

A 5 wt % solution of anisole (Sigma-Aldrich Co. LLC, St. Louis, Mo.; 99.7% purity, Catalog #296295) in ethanol was fed into the reactor (see reactor details in Section IV) with a 100 □L bed of 10 wt % Pt on ferrierite catalyst, prepared as described in Example 4, at an LHSV of about 3 $h^{-1}$. The feed was initially stabilized for about 1 hour at about 22° C. before the temperature was raised to about 300° C. and gas flow begun. Hydrogen was supplied at about 16 molar equivalents, nitrogen was supplied at about 10 NmL/min, and the total gas pressure was about 30 bar. The system was initially stabilized for about 2 hours and, during that time, the effluent sent to waste. The effluent was subsequently collected for a period of about 16 hours and analyzed by GC to give an average of the product distribution over the run time. The product contained about 96 vol. % phenol.

Example 9 (Comparative)

A 5 wt % solution of 2,6-dimethoxyphenol (Sigma-Aldrich Co. LLC, St. Louis, Mo.; 97% purity; Catalog #W313718) in ethanol:water (95:5 vol. %/vol. %) was fed into the reactor (see reactor details in Section IV) with a 100 □L bed of the 10 wt % Mo and 1 wt % W promoter on alumina catalyst, prepared as in Example 1, at an LHSV of about 3 $h^{-1}$. The feed was stabilized for about 1 hour at about 22° C. before the temperature was raised to about 325° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent was sent to waste. The effluent was subsequently collected for a period of about 16 hours and analyzed by GC to give an average product distribution over the run time. The product contained about 5 vol. % of simple aromatic compounds.

Example 10

A 5 wt % solution of eugenol (Acros Organics, Geel, Belgium; 99% purity; Catalog #: 119115000) in ethanol/ water (95:5 vol. %/vol. %) was fed into the reactor (see reactor details in Section IV) with a 200 □L bed of 10 wt % Pt on ferrierite catalyst, prepared as in Example 4, at an LHSV of about 1.5 h$^{-1}$. The feed was initially stabilized for about 1 hour at about 22° C. before the temperature was raised to about 300° C. and gas flow begun. Hydrogen was supplied at about 16 molar equivalents, nitrogen was supplied at about 10 NmL/min, and the total gas pressure was about 30 bar. The system was initially stabilized for about 2 hours and, during that time, the effluent was sent to waste. The effluent was subsequently collected for a period of about 16 hours and analyzed by GC to give an average of the product distribution over the run time. The product contained about 100 vol. % simple aromatic compounds.

Example 11

A 5 wt % solution of eugenol (Acros Organics, Geel, Belgium; 99% purity; Catalog #: 119115000) in ethanol/water (95:5 vol. %/vol. %) was fed into the reactor (see reactor details in Section IV) with a 200 □L bed of 10 wt % Ni on H-ZSM-5 catalyst, prepared as in Example 5, at an LHSV of about 1.5 h$^{-1}$. The feed was initially stabilized for about 1 hour at about 22° C. before the temperature was raised to about 300° C. and gas flow begun. Hydrogen was supplied at about 16 molar equivalents, nitrogen was supplied at about 10 NmL/min, and the total gas pressure was about 30 bar. The system was initially stabilized for about 2 hours and, during that time, the effluent was sent to waste. The effluent was subsequently collected for a period of about 16 hours and analyzed by GC to give an average of the product distribution over the run time. The product contained about 93 vol. % simple aromatic compounds.

Example 12

A 5 wt % solution of eugenol (Acros Organics, Geel, Belgium; 99% purity; Catalog #: 119115000) in ethanol/water (95:5 vol. %/vol. %) was fed into the reactor (see reactor details in Section IV) with a 200 □L bed of 10 wt % Cu on H-ZSM-5 catalyst, prepared as in Example 5, at an LHSV of about 1.5 h$^{-1}$. The feed was initially stabilized for about 1 hour at about 22° C. before the temperature was raised to 325° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent was sent to waste. The effluent was subsequently collected for a period of about 16 hours and analyzed by GC to give an average of the product distribution over the run time. The product contained about 95 vol. % simple aromatic compounds.

Example 13

A 5 wt % solution of eugenol (Acros Organics, Geel, Belgium; 99% purity; Catalog #: 119115000) in ethanol/water (95:5 vol. %/vol. %) was fed into the reactor (see reactor details in Section IV) with a 100 □L bed of 5 wt % Pt on silica catalyst, prepared as in Example 2, at an LHSV of about 3 h$^{-1}$. The feed was initially stabilized for about 1 hour at about 22° C. before the temperature was raised to 300° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent was sent to waste. The effluent was subsequently collected for a period of about 16 hours and analyzed by GC to give an average of the product distribution over the run time. The product contained about 97 vol. % simple aromatic compounds.

Example 14

A 5 wt % solution of eugenol (Acros Organics, Geel, Belgium; 99% purity; Catalog #: 119115000) in ethanol/water (95:5 vol. %/vol. %) was fed into the reactor (see reactor details in Section IV) with a 100 □L bed of 10 wt % Ni and 2 wt % Sn promoter on alumina catalyst, prepared as in Example 6, at an LHSV of about 3 h$^{-1}$. The feed was initially stabilized for about 1 hour at about 22° C. before the temperature was raised to 300° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent was sent to waste. The effluent was subsequently collected for a period of about 16 hours and analyzed by GC to give an average of the product distribution over the run time. The product contained about 92 vol. % simple aromatic compounds.

Example 15

A solution of 5 wt % eugenol (Acros Organics, Geel, Belgium; 99% purity; Catalog #: 119115000) and 2.5 wt % 2,6-dimethoxyphenol (Sigma-Aldrich Co. LLC, St. Louis, Mo.; 97% purity; Catalog #W313718) in ethanol/water (95:5 vol. %/vol. %) was fed into the reactor (see reactor details in Section IV) with a 100 □L bed of 10 wt % Pt on ferrierite, prepared as in Example 4, at an LHSV of about 3 h$^{-1}$. The feed was initially stabilized for about 1 hour at about 22° C. before the temperature was raised to about 325° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent was sent to waste. The effluent was subsequently collected for a period of about 16 hours and analyzed by GC to give an average of the product distribution over the run time. The product contained about 49 vol. % simple aromatic compounds.

Example 16

A solution of 5 wt % eugenol (Acros Organics, Geel, Belgium; 99% purity; Catalog #: 119115000) and 2.5 wt % 2,6-dimethoxyphenol (Sigma-Aldrich Co. LLC, St. Louis, Mo.; 97% purity; Catalog #W313718) in ethanol/water (95:5 vol. %/vol. %) was fed into the reactor (see reactor details in Section IV) with a 200 □L bed of 10 wt % Pt on H-ZSM-5, prepared as in Example 5, at an LHSV of about 1.5 h$^{-1}$. The feed was initially stabilized for about 1 hour at about 22° C. before the temperature was raised to about 325° C. and gas flow begun. Hydrogen was supplied at about 16 molar equivalents, nitrogen was supplied at about 10 NmL/min, and the total gas pressure was about 30 bar. The system was stabilized for about 2 hours and, during that time, the effluent sent to waste. The effluent was subsequently collected for a period of about 16 hours and analyzed by GC to give an average of the product distribution over the run time. The product contained about 93 vol. % simple aromatic compounds.

Example 17

A solution of 5 wt % eugenol (Acros Organics, Geel, Belgium; 99% purity; Catalog #: 119115000) and 2.5 wt %

2,6-dimethoxyphenol (Sigma-Aldrich Co. LLC, St. Louis, Mo.; 97% purity; Catalog #W313718) in ethanol/water (95:5 vol. %/vol. %) was fed into the reactor (see reactor details in Section IV) with a 100 □L bed of 10 wt % Pt and 2 wt % Mg promoter on silica catalyst, prepared as in Example 3, at an LHSV of about 3 h$^{-1}$. The feed was initially stabilized for about 1 hour at about 22° C. before the temperature was raised to 325° C. and gas flow begun. Hydrogen was supplied at about 16 molar equivalents, nitrogen was supplied at about 10 NmL/min, and the total gas pressure was about 30 bar. The system was initially stabilized for about 2 hours and effluent was sent to waste. The effluent was subsequently collected for a period of about 16 hours and analyzed by GC to give an average of the product distribution over the run time. The product contained about 95 vol. % simple aromatic compounds.

Example 18

Lignin is depolymerized to produce lignin monomers, which are then dissolved in an ethanol/water solution to make a 5 wt % solution. The solution is fed into a reactor (see details in Section IV) with a 200 □L bed of 10 wt % Pt on ferrierite catalyst, prepared as in Example 4, at an LHSV of about 1.5 h$^{-1}$. Hydrogen is supplied at about 16 molar equivalents, the nitrogen supply is about 10 NmL/min, and the total gas pressure is about 30 bar. The product contains greater than about 90 vol. % simple aromatics.

IV Test and Calculation Procedures

Reactor: The conversions were carried out in a flow reactor system with a maximum catalyst bed volume of about 0.2 mL. The system comprised temperature and mass flow controllers and was supplied with separate liquid and gas feeds that were mixed together before reaching the catalyst bed. The gas feed was composed of molecular nitrogen ($N_2$) and helium (He), which was added as an internal standard for the gas chromatograph (GC) analysis. The liquid feed was fed to the top of the reactor while controlling the pump pressure to about 360 psig to overcome any pressure drop from the catalyst bed. Quartz or stainless steel reactors with an aspect ratio (i.e., length/diameter) of 75 were used.

Various catalyst beds and gas feed flows were used resulting in a range of space velocities (reported in the Results section herein). The reactor effluent was also connected to another nitrogen dilution line, which diluted the effluent by a factor of two. The helium internal standard normalized any variation in this dilution for analytical purposes. The condensed products were collected by a liquid sampling system cooled to between 6.5° C. to 10° C. while the gaseous products accumulated on the overhead space of a collection vial.

The feed was equilibrated for 1 hour, after which time the liquid sample was collected for 16 hours and analyzed at the end of the experiment by offline GC. The products were analyzed online twice by GC and reported as an average. Products were analyzed by an Interscience Compact gas chromatography (GC) system (Interscience BV, Breda, the Netherlands) using three detectors (one flame ionization detector—FID—and two thermal conductivity—TCD—detectors "A" and "B," referred to hereinafter as "TCD-A" and "TCD-B," respectively). The gaseous products were reported as an average given by two sequential GC chromatograms.

The TCD-A column was an Rt-Q Bond (Restek Corp., Bellefonte, Pa.), having 26 m in length and an I.D. of 0.32 mm with a film thickness of 10 μm and using a pre-column of 2 m. The pressure was set to 150 kPa, with a split flow of 10 mL/min. The column oven temperature was set to 100° C. with a vale oven temperature of 50° C. The flow was set to 5.0 mL/min, with a carrier gas of helium. The TCD-B column was a Mol sieve MS5A (Restek Corp., Bellefonte, Pa.), having a length of 21 m and a film thickness of 10 μm and using a pre-column of 2 m. The pressure was set to 200 kPa, with a split flow of 10 mL/min. The column oven temperature was set to 70° C. with a vale oven temperature of 50° C. The flow was set to 2.0 mL/min, with a carrier gas of argon. The FID column was an RTx-624 (Restek, Bellefonte, Pa.), having a length of 28 m and an inner diameter of 0.25 mm with a film thickness of 14 mm and using a pre-column of 2 m. The pressure was set to 100 kPa, with a split flow to 20 mL/min. The column oven temperature was set to 45° C. with a vale oven temperature of 50° C.

BET Surface Area and Total Pore Volume: The BET specific surface area and total pore volume are measured using the nitrogen adsorption technique, such as that described in ASTM D 4820-99, the substance of which is herein incorporated by reference, by multipoint nitrogen adsorption, at about 77K with a Coulter SA3100 Series Surface Area and Pore Size Analyzer manufactured by Coulter Corp., of Miami, Fla. As it will be appreciated, other instrumentation can be substituted for the BET measurements as is known in the art.

Bio-based Content: The bio-based content of a material is measured using the ASTM D6866 method, which allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, which represents a small, but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide, which causes the release of carbon dioxide back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "bio-based content" is built on the same concepts as radiocarbon dating, but without use of the age equations. The analysis is performed by deriving a ratio of the amount of radiocarbon ($^{14}C$) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), preferably at least about 99 pMC, for example, about 100 pMC.

Combining fossil carbon with present day carbon into a material will result in a dilution of the present day pMC content. By presuming that 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein was done in accordance with ASTM D6866, particularly with Method B. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-component "present" in the material, not the amount of bio-material "used" in the manufacturing process.

Other techniques for assessing the bio-based content of materials are described in U.S. Pat. Nos. 3,885,155, 4,427,884, 4,973,841, 5,438,194, and 5,661,299, and WO 2009/155086, each incorporated herein by reference.

V Results

The foregoing description is given for clearness of understanding only, and no unnecessary information should be understood therefrom, as modification within the scope of the invention may be apparent to those having ordinary skill in the art.

Table 1 below shows the results for the conversion of anisole to phenol described in 2 examples. In each example, the LHSV was about 3 $h^{-1}$, anisole was as a 5 wt % solution in ethanol, and the amount of hydrogen used was about 16 molar equivalents. Comparative Example 7 used a temperature of 250° C., which was optimum for the catalyst. Example 8 used a temperature of 300° C., which was optimum for the 10 wt % Pt on ferrierite catalyst.

TABLE 1

| Example # | Anisole, [vol. %] | Phenol, [vol. %] |
|---|---|---|
| 7 (Comparative) | 55 | 25 |
| 8 | 0 | 96 |

The results in Table 1 provide a comparison of the conversion of anisole to phenol (which is a simple aromatic compound) by a catalyst according to the invention (i.e., Example 9) and that not according to the invention (i.e., Example 7). Among other things, under the same or similar reaction conditions, the catalysts according to the invention resulted in far greater conversion of anisole to phenol.

Table 2 shows in a tabulated form the conversion of methoxylated aromatic compounds to simple aromatic compounds using the catalysts and processes of this disclosure.

TABLE 2

| Example # | Catalyst Preparation Example # | Feed | Simple Aromatics, [vol. %] |
|---|---|---|---|
| 9 (Comparative) | 1 | 2,6-dimethoxyphenol | 5 |
| 10 | 4 | Eugenol | 100 |
| 11 | 5 | Eugenol | 93 |
| 12 | 5 | Eugenol | 95 |
| 13 | 2 | Eugenol | 97 |
| 14 | 6 | Eugenol | 92 |
| 15 | 4 | Eugenol + 2,6-dimethoxyphenol | 49 |
| 16 | 5 | Eugenol + 2,6-dimethoxyphenol | 93 |
| 17 | 3 | Eugenol + 2,6-dimethoxyphenol | 95 |

The results in Table 2 show that the catalysts according to the invention (i.e., Examples 10 through 17) give conversion of methoxylated aromatic compounds, such as eugenol, 2,6-dimethoxyphenol, or mixtures thereof, to simple aromatic compounds. However, catalysts such as molybdenum sulfide, with or without promoter metals (i.e., Example 9 with catalyst prepared as in Example 1), under similar reaction conditions produce only small amounts of simple aromatic compounds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for the conversion of a composition of depolymerized lignin to simple aromatic compounds comprising contacting said composition of depolymerized lignin with a catalyst and about 32 molar equivalents of hydrogen in a flow reactor, wherein said catalyst comprises Ni deposited onto ferrierite zeolite; and wherein said flow reactor has a temperature of about 350° C., a pressure of about 370 psig, and a Liquid Hourly Space Velocity of about 3 $h^{-1}$.

2. A process for the conversion of a composition of depolymerized lignin to simple aromatic compounds comprising contacting said composition of depolymerized lignin with a catalyst and about 8 to about 64 molar equivalents of hydrogen in a flow reactor, wherein said catalyst comprises Ni deposited onto ferrierite zeolite; and wherein said flow reactor has a temperature between about 250° C. and about 400° C., a pressure between about 150 psig and about 500 psig, and a Liquid Hourly Space Velocity of less than about 10 $h^{-1}$.

3. The process of claim 2, wherein said Ni comprises less than about 20 wt % of said catalyst.

4. The process of claim 2, wherein said simple aromatic compounds have a bio-based content greater than about 30%.

5. A process for the conversion of a composition of depolymerized lignin to simple aromatic compounds comprising contacting said composition of depolymerized lignin with a catalyst and about 8 to about 64 molar equivalents of hydrogen in a flow reactor, wherein said catalyst comprises Pt deposited onto an H-ZSM-5 zeolite; and wherein said flow reactor has a temperature between about 250° C. and about 400° C., a pressure between about 150 psig and about 500 psig, and a Liquid Hourly Space Velocity of less than about 10 $h^{-1}$.

6. The process of claim 5, wherein said Pt comprises less than about 20 wt % of said catalyst.

7. The process of claim 2, wherein said simple aromatic compounds have a bio-based content greater than about 30%.

* * * * *